United States Patent [19]

Sanjiki et al.

[11] 4,346,096
[45] Aug. 24, 1982

[54] ANTITUMOR AND IMMUNOSUPPRESSIVE 4-CARBAMOYL IMIDAZOLIUM-5-OLATE DERIVATIVES AND PHARMACEUTICAL COMPOSITION THEREOF

[75] Inventors: Tetsutaro Sanjiki, Ibaraki; Akinori Seta, Toyonaka; Takao Kiyohara, Takarazuka, all of Japan

[73] Assignee: Sumitomo Chemical Company, Limited, Osaka, Japan

[21] Appl. No.: 176,241

[22] Filed: Aug. 7, 1980

[30] Foreign Application Priority Data

Sep. 20, 1979 [JP] Japan .................... 54-121783

[51] Int. Cl.³ ............... C07D 233/64; C07D 233/28; C07D 233/66; A61K 31/415
[52] U.S. Cl. .................. 424/273 R; 548/337; 260/239.9
[58] Field of Search ............... 548/343, 337; 424/273 R; 260/239.9

[56] References Cited

U.S. PATENT DOCUMENTS 2,373,298  3/1942  Dougherty et al. .......... 260/456 P
4,140,788  2/1979  Atsumi et al. ............... 548/337

FOREIGN PATENT DOCUMENTS 50-121276  9/1974  Japan .................... 548/337
53-5162    1/1978  Japan .................... 548/337
53-53652   5/1978  Japan .................... 548/337

OTHER PUBLICATIONS

Mizuno, et al., Journal of Antibiotics, 27, 775 (1974).
Schipper, et al., J.A.C.S., 74, 350 (1952).
Sakaguchi, et al., Journal of Antibiotics, 28, 798 (1975).
Tsujino, et al., Proceedings IAMS, 3, 441 (1974).
Miller, et al., J.A.C.S., 74, 2892 (1952).
Sakaguchi, et al., Cancer Research, 35, 1643 (1975).
Sakaguchi, et al., Proceedings IAMS, 3, 539 (1976).

Primary Examiner—John M. Ford
Assistant Examiner—Robert C. Whittenbaugh
Attorney, Agent, or Firm—Wenderoth, Lind & Ponack

[57] ABSTRACT

There are provided compounds of the formula:

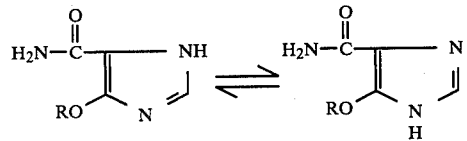

wherein R is an alkyl sulfonyl group or a benzenesulfonyl group which may be substituted with a lower alkyl group, a lower alkoxy group, a nitro group or a halogen atom, and a process producing them, useful as antitumor agents and immunosuppressants.

10 Claims, No Drawings

ANTITUMOR AND IMMUNOSUPPRESSIVE 4-CARBAMOYL IMIDAZOLIUM-5-OLATE DERIVATIVES AND PHARMACEUTICAL COMPOSITION THEREOF

The present invention relates to novel 4-carbamoylimidazolium-5-olate derivatives and a process for the preparation thereof. More particularly, the present invention pertains to 4-carbamoylimidazolium-5-olate derivatives useful as antitumor agents and immunosuppressants, a pharmaceutical composition containing at least one of them, and a process for preparing them.

It has been known that the compounds of the following formula (IV) have antitumor and immunosuppressive activity (Japanese Patent Publication (Kokai) No. 53-5162, 53-53652),

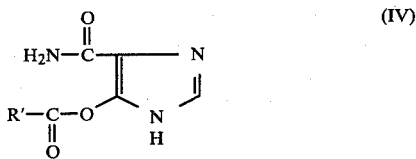
(IV)

wherein R' is an alkyl group, an adamantyl group or a phenyl group which may be substituted with an alkyl group, an alkoxy group, an alkylthio group, a halogen atom, a nitro group, a cyano group, a methylenedioxy group or an acetamido group.

The compounds of the formula (IV) are practically insoluble in aqueous media, therefore their use in therapy may be restricted.

We have carried out an extensive study seeking new derivatives which are soluble in aqueous media and have now found the novel imidazole derivatives of the present invention.

The novel imidazole derivatives of the present invention are those represented by the following formula (I),

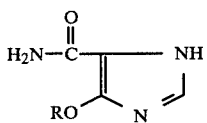
(I)

wherein R is an alkyl sulfonyl group; a benzenesulfonyl group which may be substituted with a lower alkyl group, a lower alkoxy group, a nitro group or a halogen atom.

As used herein, the term "lower alkyl" means a straight or branched alkyl having 1 to 6 carbon atoms (e.g. methyl, ethyl, n-propyl, isopropyl, n-butyl, n-hexyl).

The term "lower alkoxy" means a straight or branched alkoxy having 1 to 6 carbon atoms (e.g. methoxy, ethoxy, n-propoxy, n-butoxy, isobutoxy, t-butoxy, n-hexyloxy).

The term "halogen" means fluorine, chlorine, bromine and iodine.

The term "alkyl" means a straight or branched alkyl having 1 to 18 carbon atoms (e.g. methyl, ethyl, n-propyl, isopropyl, n-butyl, isobutyl, t-butyl, pentyl, hexyl, heptyl, octyl, nonyl, decyl, hexadecyl, octadecyl).

The compound of the formula (I) of the present invention can be prepared by reacting 4-carbamoylimidazolium-5-olate (II),

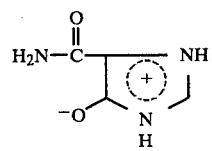
(II)

or its reactive derivative, with a reactive derivative of a sulfonic acid of the formula (III),

R—OH     (III)

wherein R is as defined above.

Examples of preferred reactive derivatives of sulfonic acids of the formula (III) are sulfonic acid halides (e.g. chlorides, bromides, iodides, fluorides), activated intermediates prepared by reacting sulfonic acids with reaction products obtained from N,N-dimethylformamide and oxalyl chloride (or phosgene or thionyl chloride or phosphorus pentachloride) and the like.

Examples of preferred reactive derivatives of 4-carbamoylimidazolium-5-olate of the formula (II) are trimethylsilyl derivatives, trialkyltin derivatives, mercury salts, silver salts and the like.

Typical examples of preferred solvents which may be used in this reaction are methylene chloride, chloroform, pyridine, diethyl ether, tetrahydrofuran, dioxane, benzene, toluene, methanol, ethanol, N,N-dimethylformamide, formamide, N,N-dimethylacetamide, acetonitrile, nitromethane, acetone, and ethyl acetate.

The reaction can generally be effected at a reaction temperature from −78° to 100° C., preferably from −60° to 60° C.

The reaction of 4-carbamoylimidazolium-5-olate with sulfonic acid halides can usually be carried out in an inert polar solvent or a mixture of water and inert organic solvent, preferably in the presence of an inorganic or organic base, at a temperature from −10° to 60° C. using one to two mole equivalents of the acid halide.

Typical examples of said inert polar solvents are tetrahydrofuran, dioxane, pyridine, N,N-dimethylformamide, formamide, N,N-dimethylacetamide and dimethylsulfoxide. Typical examples of said inert organic solvents are tetrahydrofuran, dioxane, diethyl ether, chloroform, dichloromethane, dichloroethane, benzene, toluene, and xylene. Examples of preferred inorganic base are sodium hydroxide, sodium carbonate, sodium bicarbonate, potassium carbonate or bicarbonate and potassium hydroxide. Examples of preferred organic base are pyridine, triethylamine and N,N-dimethylaniline.

The reaction of 4-carbamoylimidazolium-5-olate with the above-mentioned activated intermediates can usually be carried out in an organic solvent (e.g. acetonitrile, pyridine, N,N-dimethylformamide, N,N-dimethylacetamide, chloroform) at a temperature from −78° to 80° C.

The compounds of the formula (I) can also be prepared by reacting a silylated derivative of 4-carbamoylimidazolium-5-olate with reactive derivatives of sulfonic acids (e.g. acid halides) at a temperature from −78° to 50° C. in an inert organic solvent (e.g. dimethylformamide, tetrahydrofuran, dioxane, diethyl ether, benzene, toluene).

The silylated derivatives of 4-carbamoylimidazolium-5-olate are known and can be prepared by known methods (Hayashi, et al. Japanese Patent Publication (Kokai) No. 50-121276).

When the compounds of the formula (I) exist in the form of their silylated derivative in the reaction mixture they can be subjected to a desilylation reaction with desilylating reagents (e.g. acetic acid, methanol).

When the reactive derivative of the acid (III) is acid halide, the eliminated halide can be neutralized by an organic base (e.g. triethylamine, pyridine).

The compounds of the formula (I) can be isolated and purified by known purification methods (e.g. recrystallization, column chromatography).

The imidazole derivatives of the present invention may exist in a mixture of the two tautomers as follows:

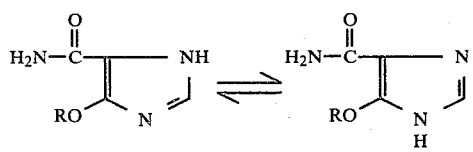

both of which are within the scope of the present invention.

The compounds of the present invention possess potent antitumor activities against Sarcoma 180, Lewis Lung Carcinoma, Ehrlich Carcinoma, P-388 Leukemia and the like. The compounds of the formula (I) are useful as antitumor agents, and they exhibit particularly excellent inhibitory effects against tumors and also exhibit a prolonging effect on the life span.

The antitumor activities of the compounds of the present invention were estimated according to the methods described in "Cancer chemotherapy reports" Part 3, Vol. 3 (no. 2) p. 13 (1972). The results are given in the following Table 1.

TABLE 1

| | Antitumor effect on mouse experimental tumors | | |
|---|---|---|---|
| Compound | Dose (mg/kg) Route i.p. | Schedule | Inhibition Ratio (%) Lewis Lung Carcinoma (solid) |
| 5-Carbamoyl-1H-imidazole-4-yl benzenesulfonate | 100 | 9qd | 44.1 |
| 5-Carbamoyl-1H-imidazole-4-yl 4'-fluorobenzenesulfonate | 50 | 9qd | 48.2 |

$BDF_1$ male mice, 5 weeks old, weighing between 18 and 22 g., were used. Each test group was composed of 6–7 mice. Two million cells of Lewis Lung Carcinoma were injected in the hind leg. The drug was administered intraperitoneally at day 1, 3, 5, 7 and 9 (or 5q2d) or at days 1 to 9 (or 9qd).

After killing the mice at day 13, tumors were removed and weighed. The tumor inhibitory ratio was calculated according to the following formula.

$$\text{Inhibition ratio} = \left(1 - \frac{\text{the mean tumor weights of treated group}}{\text{the mean tumor weights of control group}}\right) \times 100$$

The compounds of the present invention also possess excellent immunosuppressive activity as well as potent antitumor activity.

The compounds (I) of the present invention have low toxicity. They do not show any toxic symptoms, even when over 1000 mg/kg of the compounds are orally administered to a mouse. Moreover, they do not exhibit the influence of decreasing peripheral leucocytes, which is one of the most serious side effects of immunosuppressants.

The compounds of the present invention can be administered orally or parenterally to a warm-blood animal at a daily dose of 2–200 mg/kg as an antitumor agent, and 1–100 mg/kg as an immunosuppressant agent in a conventional dosage unit form.

The compounds of the present invention are made up alone or together with a conventional pharmaceutical carrier or diluent into a conventional solid or liquid pharmaceutical preparation (e.g. powders, granules, tablets, capsules, suspensions, emulsions, solutions) using the conventional methods in the pharmaceutical field. For example, tablets or capsules contain 50–500 mg of the compounds. Especially, the compounds (I) of the present invention can be used for an injection and an i.v. drop since they are water soluble.

The following examples are given to illustrate the present invention more precisely but it is not intended to limit the present invention thereto.

EXAMPLE 1

To a suspension of 0.636 g. of 4-carbamoylimidazolium-5-olate in 15 ml of dry pyridine was added 0.80 ml of benzenesulfonyl chloride at a temperature below 5° C. and stirring was continued for an hour at a temperature below 5° C. and for 20 hours at room temperature. To the reaction mixture was added 0.9 ml of triethylamine and separated salts were filtered off. The filtrate was concentrated under reduced pressure. To the residue was added chloroform and then separated crystals were filtered off, washed with chloroform and diethyl ether and dried to give 1.22 g. of 5-carbamoyl-1H-imidazole-4-yl benzenesulfonate.

0.530 g. of crude material was recrystallized from N,N-dimethylformamide and water. Amount: 0.400 g. m.p.: 147.5°–148.0° C.

$\nu_{max}^{nujol}$ (cm$^{-1}$): 3470, 1680, 1610, 1580, 1420, 1190, 1090, 950, 820.

| Elemental analysis: | C (%) | H (%) | N (%) | S (%) |
|---|---|---|---|---|
| Calculated for $C_{10}H_9N_3O_4S$ | 44.93 | 3.39 | 15.72 | 12.00 |
| Found | 45.4 | 3.6 | 15.6 | 11.41 |

EXAMPLE 2

Following a procedure similar to that of Example 1 but using 0.636 g. of 4-carbamoylimidazolium-5-olate and 1.240 g. of p-toluenesulfonyl chloride there was obtained 1.24 g. of 5-carbamoyl-1H-imidazole-4-yl 4'-methylbenzenesulfonate.

0.510 g. of crude material was recrystallized from N,N-dimethylformamide and water. Amount: 0.440 g. m.p.: 153° C. (dec.)

$\nu_{max}^{nujol}$ (cm$^{-1}$): 3450, 3150, 1660, 1605, 1420, 1190, 1170, 1080, 949

| Elemental analysis: | C (%) | H (%) | N (%) | S (%) |
|---|---|---|---|---|
| Calculated for $C_{11}H_{11}N_3O_4S$ | 46.79 | 3.94 | 14.89 | 11.36 |
| Found | 46.77 | 3.94 | 14.76 | 11.21 |

EXAMPLE 3

Following a procedure similar to that of Example 1 but using 0.636 g. of 4-carbamoylimidazolium-5-olate and 1.372 g. of p-chlorobenzenesulfonyl chloride and stirring for an hour at 45° C. after being stirred for 20 hours at room temperature there was obtained 0.700 g. of 5-carbamoyl-1H-imidazole-4-yl 4'-chlorobenzenesulfonate.

The crude material was recrystallized from N,N-dimethylformamide and water. Amount: 0.595 g. m.p.: 158° C. (dec.)

$v_{max}^{nujol}$ (cm$^{-1}$): 3470, 1660, 1610, 1570, 1420, 1190, 1170, 1090, 1010, 945

| Elemental analysis: | C (%) | H (%) | N (%) | S (%) | Cl (%) |
|---|---|---|---|---|---|
| Calculated for $C_{10}H_8N_3O_4SCl$ | 39.80 | 2.67 | 13.93 | 10.63 | 11.75 |
| Found | 39.6 | 2.5 | 13.8 | 10.70 | 12.00 |

EXAMPLE 4

Following a procedure similar to that of Example 3 but using 0.636 g. of 4-carbamoylimidazolium-5-olate and 1.44 g. of o-nitrobenzenesulfonyl chloride there was obtained 1.09 g. of 5-carbamoyl-1H-imidazole-4-yl 2'-nitrobenzenesulfonate.

0.520 g. of crude material was recrystallized from N,N-dimethylformamide and water. Amount: 0.470 g. m.p.: 171.5°–174.0° C.

$v_{max}^{nujol}$ (cm$^{-1}$): 3470, 1670, 1610, 1550, 1420, 1195, 1100, 950

| Elemental analysis: | C (%) | H (%) | N (%) | S (%) |
|---|---|---|---|---|
| Calculated for $C_{10}H_8N_4O_6S$ | 38.46 | 2.58 | 17.94 | 10.27 |
| Found | 38.3 | 2.5 | 18.0 | 10.17 |

EXAMPLE 5

Following a procedure similar to that of Example 1 but using 0.636 g. of 4-carbamoylimidazolium-5-olate and 1.343 g. of p-methoxybenzenesulfonyl chloride there was obtained 1.31 g. of 5-carbamoyl-1H-imidazole-4-yl 4'-methoxybenzenesulfonate.

0.500 g. of crude material was recrystallized from methanol and water. Amount: 0.230 g. m.p.: 162°–164° C.

$v_{max}^{nujol}$ (cm$^{-1}$): 3400, 1660, 1315, 1270, 1190, 1165, 1090, 1015, 945

| Elemental analysis: | C (%) | H (%) | N (%) | S (%) |
|---|---|---|---|---|
| Calculated for $C_{11}H_{11}N_3O_5S$ | 44.43 | 3.73 | 14.14 | 10.79 |
| Found | 44.2 | 3.5 | 14.0 | 10.41 |

EXAMPLE 6

Following a procedure similar to that of Example 1 but using 0.636 g. of 4-carbamoylimidazole-5-olate and 0.50 ml of methanesulfonyl chloride there was obtained 0.64 g. of 5-carbamoyl-1H-imidazole-4-yl methanesulfonate after recrystallization from N,N-dimethylformamide and chloroform. m.p.: 174°–175° C.

$v_{max}^{nujol}$ (cm$^{-1}$): 3450, 3160, 1670, 1605, 1570, 1430, 1180, 1170, 1100, 980, 940.

| Elemental analysis: | C (%) | H (%) | N (%) | S (%) |
|---|---|---|---|---|
| Calculated for $C_5H_7N_3O_4S$ | 29.23 | 3.44 | 20.56 | 15.61 |
| Found | 29.06 | 3.40 | 20.45 | 15.31 |

EXAMPLE 7

To a suspension of 1.272 g. of 4-carbamoylimidazolium-5-olate in 20 ml of dry pyridine was added 2.1 g. of p-fluorobenzenesulfonyl chloride at room temperature. Stirring was continued at room temperature overnight. To the reaction mixture was added 1.5 ml of triethylamine and separated salts were filtered off. The filtrate was concentrated under reduced pressure. To the residue was added diethyl ether and then separated crystals were filtered off and dried to give 3.04 g. of 5-carbamoyl-1H-imidazole-4-yl p-fluorobenzenesulfonate.

The crude material was recrystallized from methanol. m.p.: 159°–160° C.

$v_{max}^{nujol}$ (cm$^{-1}$): 3510, 3405, 1680, 1600, 1580, 1500, 1380, 1365, 1200, 1160, 1105, 1095

| Elemental analysis: | C (%) | H (%) | N (%) | S (%) |
|---|---|---|---|---|
| Calculated for $C_{10}H_8N_3O_4SF$ | 42.10 | 2.83 | 14.73 | 11.24 |
| Found | 41.95 | 2.72 | 14.44 | 10.98 |

According to the present invention, there are obtained, for example, the following compounds:
- 5-carbamoyl-1H-imidazole-4-yl ethanesulfonate,
- 5-carbamoyl-1H-imidazole-4-yl propane-1'-sulfonate,
- 5-carbamoyl-1H-imidazole-4-yl butane-1'sulfonate,
- 5-carbamoyl-1H-imidazole-4-yl pentane-1'-sulfonate,
- 5-carbamoyl-1H-imidazole-4-yl hexane-1'-sulfonate,
- 5-carbamoyl-1H-imidazole-4-yl decane-1'-sulfonate,
- 5-carbamoyl-1H-imidazole-4-yl hexadecane-1'-sulfonate,
- 5-carbamoyl-1H-imidazole-4-yl octadecane-1'-sulfonate.

What is claimed is:

1. A compound of the formula $$H_2N-\overset{O}{\overset{\|}{C}}-\underset{RO}{\overset{}{\diagdown}}\underset{N}{\overset{NH}{\diagup}} \quad \text{or} \quad H_2N-\overset{O}{\overset{\|}{C}}-\underset{RO}{\overset{}{\diagdown}}\underset{\underset{H}{N}}{\overset{N}{\diagup}}$$

wherein R is a benzenesulfonyl group which may be substituted with a lower alkyl group, a lower alkoxy group, a nitro group or a halogen atom.

2. A compound according to claim 1, wherein R is benzenesulfonyl.

3. A compound according to claim 1, wherein R is p-toluenesulfonyl.

4. A compound according to claim 1, wherein R is p-chlorobenzenesulfonyl.

5. A compound according to claim 1, wherein R is o-nitrobenzenesulfonyl.

6. A compound according to claim 1, wherein R is p-methoxybenzenesulfonyl.

7. A compound according to claim 1, wherein R is p-fluorobenzenesulfonyl.

8. An immunosuppressant composition which comprises an amount of a compound of claim 1 as an active ingredient and a pharmaceutically acceptable carrier or diluent.

9. A pharmaceutical antitumor composition which comprises a compound of claim 1 as an active ingredient in an amount which is effective for treating Sarcoma 180, Lewis Lung Carcinoma, Ehrlich Carcinoma or P-388 Leukemia, and a pharmaceutically acceptable carrier or diluent.

10. A pharmaceutical antitumor composition which comprises a compound of claim 1 as an active ingredient in an amount which is effective for treating Lewis Lung Carcinoma, and a pharmaceutically acceptable carrier or diluent.

* * * * *